(12) United States Patent
Keller et al.

(10) Patent No.: US 7,083,923 B2
(45) Date of Patent: Aug. 1, 2006

(54) HIGH-THROUGHPUT GLUTATHIONE S-TRANSFERASE POLYMORPHIC ALLELE ASSAY DESIGN

(75) Inventors: Charles Keller, Salt Lake City, UT (US); Linda Ballard, Salt Lake City, UT (US); Richard Lemmons, Salt Lake City, UT (US); Francis Ali-Osman, Houston, TX (US)

(73) Assignee: University of Utah Research Foundation, Salt Lake City, UT (US)

( * ) Notice: Subject to any disclaimer, the term of this patent is extended or adjusted under 35 U.S.C. 154(b) by 588 days.

(21) Appl. No.: 10/296,012

(22) PCT Filed: Jul. 20, 2001

(86) PCT No.: PCT/US01/22923

§ 371 (c)(1),
(2), (4) Date: Nov. 20, 2002

(87) PCT Pub. No.: WO02/08465

PCT Pub. Date: Jan. 31, 2002

(65) Prior Publication Data

US 2004/0023238 A1 Feb. 5, 2004

Related U.S. Application Data

(60) Provisional application No. 60/219,531, filed on Jul. 20, 2000.

(51) Int. Cl.
*C12Q 1/68* (2006.01)
*C12P 19/34* (2006.01)
*C07H 21/04* (2006.01)

(52) U.S. Cl. .................. 435/6; 435/91.2; 536/23.5; 536/24.31; 536/24.33

(58) Field of Classification Search ............. None
See application file for complete search history.

(56) References Cited

U.S. PATENT DOCUMENTS 5,888,778 A  3/1999  Shuber ................. 435/91.1
5,965,363 A  10/1999  Monforte et al. ............ 435/6

FOREIGN PATENT DOCUMENTS

GB        19738908        3/1999

OTHER PUBLICATIONS

Kristensen. Pharmacogentics. 1998. 8: 441-447.*
Lucentini. The Scientist. Dec. 2004, p. 20.*
Jourenkova-Mironova et al. International Journal of Cancer. 1999. 81: 44-48.*
Matthias et al. Cancer Epidemiology, Biomarkers and Prevention. Sep. 1999. 8: 815-823.*
"Enabling Large-Scale Pharmacogenetic Studies by High-Throughput Mutation Detection and Genotyping Technologies," Michael M. Shi, *Clinical Chemistry*, pp. 164-172, 2001.
"High-Throughput Genotyping Method for Glutathione," *Research Communications in Molecular Pathology and Pharmacology*, vol. 103, No. 1, Michael M. Shi, pp. 3-15.

* cited by examiner

*Primary Examiner*—Carla J. Myers
(74) *Attorney, Agent, or Firm*—Madson & Austin

(57) ABSTRACT

A high-throughput assay for characterizing a subject's genetic makeup is disclosed. Specifically a high-throughput assay utilizing PCR is disclosed that permits the rapid and accurate characterization of a subject's inherited alleles of the polymorphic glutathione S-transferase (GST) genes GSTM1, GSTM3, GSTP1, and GSTT1. This method allows detection of the specific alleles inherited, including the gene dosage of GSTM1 and GSTT1 while not requiring restriction endonuclease digestion of the PCR products in order to detect length differences. Further, the method allows all analyses to be performed simultaneously in the same gel lane, thus further adding efficiency and cost-effectiveness.

28 Claims, 1 Drawing Sheet

HIGH-THROUGHPUT GLUTATHIONE S-TRANSFERASE POLYMORPHIC ALLELE ASSAY DESIGN

CROSS-REFERENCE TO RELATED APPLICATION

This application is the National Stage of International Application PCT/US01/22923, filed Jul. 20, 2001, which claims the benefit of U.S. Provisional Application 60/219,531, filed Jul. 20, 2000.

STATEMENT REGARDING FEDERALLY SPONSORED RESEARCH

This invention was made with government support under NIH grant numbers 5M01RR00064 and CA 79644 awarded by the National Institutes of Health. The Government has certain rights to this invention.

BACKGROUND OF THE INVENTION

1. Field of the Invention

The present invention relates to high-throughput assays for characterizing a subject's genetic makeup. Specifically, the instant invention is a high-throughput assay that permits the rapid and accurate characterization of a subject's inherited alleles of the polymorphic glutathione S-transferase (GST) genes GSTM1, GSTM3, GSTP1, and GSTT1.

2. Background of the Invention

Recent cancer research has shown that the presence of various polymorphisms of glutathione S-transferase ("GST") correlates with altered risk for certain cancers and altered response and toxicity from currently known and used cancer treatments, including chemotherapy. The GST family of enzymes has been shown to function in the detoxification of a broad range of environmental and non-environmental DNA-damaging carcinogens such as polyaromatic hydrocarbons like those found in first- and second-hand cigarette smoke. Additionally, however, these enzymes are capable of detoxifying chemotherapeutic compounds such as alkylating agents and nanthracyclines as well as reactive oxygen species and peroxides. See S. Tsuchida and K. Sato, *Critical Reviews in Biochemistry and Molecular Biology*, 27(4, 5):337–384 (1992), and S. A. Weitzman and L. I. Gordon, *Blood*, 76(4):655–663 (1990).

This family of enzymes has been subdivided into four subclasses, including GSTM1, GSTM3, GSTP1, and GSTT1. Ali-Osman et al., *J. Biol. Chem.*, 272(15):10004–10012 (1997); Fryer et al., *Biochem. J.*, 295:313–315 (1993); Inskip et al., *Biochem. J.*, 312:713–716 (1995); and Pemble et al., *Biochem. J.*, 300: 271–276 (1995). A first of these is the GSTM1 class, which includes the following allelic variants: GSTM1*null, GSTM1*A, and GSTM1*B. Fryer et al., *Biochem. J.*, 295: 313–315 (1993).

GSTM1*null is thought to result from an unequal crossing-over at a duplicated region between the GSTM1 and the GSTM2 loci. Pearson et al., *Am. J. Hum. Genet.*, 53:220–233 (1993); and Xu et al., *J. Biol. Chem.*, 273: 3517–3527 (1998). As with other null alleles, this one produces no functional product and thus acts as a recessive gene. GSTM1*A and GSTM1*B are polymorphic alleles commonly thought to result from a C to G substitution at codon 173. This change results in a change from the $Lys^{173}$ of GSTM1*A to the $Asn^{173}$ of GSTM1*B. This change alters a hinge region between alpha helices which is involved in GSTM1 dimerization.

A second subgroup of GST enzymes is dubbed the GSTM3 class, including the GSTM3*A and GSTM3*B allelic variants. These alleles are thought to result from a 3 base-pair deletion in intron 6 which generates a YY1 negative transcription factor recognition site in GSTM3*B that does not exist in GSTM3*A.

A third such subgroup of GST enzymes is the GSTP1 group which includes GSTP1*A, GSTP1*B, and GSTP1*C. A GSTP1*D allele has been observed, but only in very rare circumstances. These polymorphic alleles result from A to G and C to T transitions at nucleotides +313 of exon 5 and +341 of exon 6, respectively. Specifically, GSTP1*A codon 104 is ATC, coding for $Ile^{104}$, and codon 113 is GCG, for $Ala^{113}$. GSTP1*B codon 104 is GTC, coding for $Val^{104}$, and codon 113 is GCG for $Ala^{113}$. GSTP1*C codon 104 is GTC, coding for $Val^{104}$, and codon 113 is GTG for $Val^{113}$. GSTP1*D codon 104 is ATC, coding for $Ile^{104}$, and codon 113 is GTG for $Val^{113}$.

A fourth group of GST enzymes is the GSTT1 subgroup, which includes GSTT1*null and GSTT1. As with the other null allele noted above, the GSTT1*null allele produces no functional product, thus operating as a recessive allele.

There are techniques extant in the art for assessing which alleles are present in an individual's genotype. Most of these assays do not allow investigators to determine gene dosages. Here, the term "gene dosage" is used to denote whether one or both alleles were present when a PCR product suggested the presence of at least one non-null allele. Further, most of the currently used assays do not differentiate between the non-null GSTM1 alleles GSTM1*A and GSTM1*B. These methods also generally require that the PCR products undergo restriction endonuclease digestion to allow the determination of genotypes, thus adding extra complexity and expense to the method.

Kristensen et al. reported one such assay in 1998. Kristensen et al., *Pharmacogenetics*, 8:441447 (1998). This assay was able to evaluate only the polymorphisms of GSTM1, GSTP1, and GSTT1, while not being capable of distinguishing between GSTM1*A and GSTM1*B. Further, when looking at GSTP1, the assay examined only codon 104, ignoring the polymorphisms showing changes at codon 113. Finally, as with other known assays, this assay method did not examine the gene dosage of either GSTM1 or GSTT1.

The availability of simple, effective assays could allow the analysis of individuals' genomes in order to detect risk for specific diseases and cancers and to allow the development of individualized prevention and/or treatment strategies. Further, in regard to the specific family of enzymes referenced above, specific, accurate assays could allow the development of tailored therapeutic regimens for patients predicted to have decreased therapeutic response to medical therapy, including cancer therapy, based on their expression of GST enzymes, or for patients predicted to have increased therapy-related toxicity. Additionally, such assays would simplify the implementation of patient-specific utilization of allele-specific small-molecule inhibitors for the purpose of reversing chemotherapy resistance among cancers, such as those over-expressing certain GST polymorphic alleles.

From the above, it is apparent that it would be an improvement in the art to provide a high-throughput assay method for rapidly, inexpensively, and accurately characterizing the GST alleles present in a subject. It would be a further advancement in the art to provide a high-throughput GST assay method which is capable of accurately determining the gene dosage of GSTM1 and GSTT1 using competitive PCR. Additionally, it would be a further advancement in the art to provide such an assay design which is simpler, faster, and cheaper than those currently known in the art because it does not require restriction endonuclease digestion of PCR products in order to elucidate the length differences between GST alleles. Similarly, it would be an improvement in the art to allow the assay of all of the PCR products simultaneously in a single gel lane, which would yield further savings in time and expense. Finally, it would be an improvement in the art to provide a high-throughput assay method that would comprehensively assay all four GST polymorphs and their alleles, including null alleles. Such an assay method is disclosed herein.

SUMMARY OF THE INVENTION

The present invention provides methods and apparatus for detecting the presence of glutathione S-transferase alleles using PCR methods and unique primers in such a way as to allow accurate genotyping by detecting the alleles of GSTM1, GSTM3, GSTT1, and GSTP1 present in a sample, while also allowing the detection of the gene dosage of GSTM1 and GSTT1.

This invention is important to the feasibility and future success of large population studies of how differences in the genotype of the alleles of glutathione S-transferase correlate with risk for cancer, as well as how the alleles correlate with possibility of risk and successful outcomes of therapy for a group of diseases including cancer. Specifically, GST enzyme polymorphisms have been correlated with risks for cancer and with risks of altered response and toxicity from cancer treatments. Existing assays for the alleles of GSTM1, GSTM3, GSTT1, and GSTP1 require multiple PCR runs followed by endonuclease digestion of the PCR products in order to detect the length differences between the GST polymorphic alleles. Most currently known and practiced assays are incapable of demonstrating the presence of the alleles of all four polymorphs. Further, both GSTM1 and GSTT1 have null alleles, and existing assays cannot show the presence of these alleles or the corresponding gene dosage of GSTM1 and GSTT1. Finally, current analysis methods are very expensive. This fact places strong restrictive limits on the size of the population evaluated in many recent studies.

The instant invention overcomes these limitations by using carefully designed PCR primers in paired PCR competitions to allow each of the alleles of the polymorphisms of GST to be detected, including both null alleles. Table 1 shows one set of possible primers that can be used with the instant invention. Forward primers are indicated by "Fwd," and reverse primers are indicated by "Rvs." TET and FAM are fluorescent tags that can be used to detect sequences by automated polyacrlamide gel electrophoresis. Boxed sequences indicate non-sequence specific tails used to create PCR product length polymorphisms. Underlined nucleotides indicate single nucleotide polymorphisms.

TABLE 1

High Throughput Genotyping: PCR Primers

| Gene | Primer name | Fwd/Rvs | Primer Sequence | | PCR Product |
|---|---|---|---|---|---|
| GSTM1 | M1F-A | Fwd | 5'-(TET)TTGGGAAGGCG TCCAAGCAC-3' | (SEQ ID NO: 1) | 142 bp (GSTM1*A) |
| | M1F-B | Fwd | 5'-(FAM)TCTTTGGGAA GGCGTCCAAGCAG-3' | (SEQ ID NO: 2) | 145 bp (GSTM1*B) |
| | M1R | Rvs | 5'-GTTTCTTCTGCTTCAC GTGTTATGAAGGTTC-3' | (SEQ ID NO: 3) | 0 bp (GSTM1*null) |
| GSTM3 | M3F | Fwd | 5'-(FAM)GTTTCTCCTCA GTACTTGGAAGAGCT-3' | (SEQ ID NO: 4) | 287 bp (GSTM3*A) |
| | M3R | Rvs | 5'-GTTTCTCACATGAAA GCCTTCAGGTT-3' | (SEQ ID NO: 5) | 284 bp (GSTM3*B) |
| GSTP1 | P1-10FA | Fwd | 5'-(FAM)GTTTCTGACCTC CGCTGCAAATACA-3' | (SEQ ID NO: 6) | 150 bp (Ile$^{104}$) |
| | P1-104FG | Fwd | 5'-(TET)GTTTCTCTTGAC CTCCGCTGCAAATACG-3' | (SEQ ID NO: 7) | 153 bp (Val$^{104}$) |
| | P1-104R | Rvs | 5'-GTTTCTCAGCCCAAGC CACCTGA-3' | (SEQ ID NO: 8) | |
| | P1-113FC | Fwd | 5'-(TET)CTTTGGTGTCTG GCAGGAGGT-3' | (SEQ ID NO: 9) | 130 bp (Ala$^{113}$) |
| | P1-113FT | Fwd | 5'-(FAM)GGTGTCTGGCA GGAGGC-3' | (SEQ ID NO: 10) | 126 bp (Val$^{113}$) |
| | P1-113R | Rvs | 5'-GTTTCTTGGTCTCCCA CAATGAAGG-3' | (SEQ ID NO: 11) | |

TABLE 1-continued

High Throughput Genotyping: PCR Primers

| Gene | Primer name | Fwd/Rvs | Primer Sequence | | PCR Product |
|---|---|---|---|---|---|
| GSTT1 | T1F | Fwd | 5'-(FAM)TTCCTTACTGGT CCTCACATCTC-3' | (SEQ ID NO: 12) | 255 bp (GSTT1) |
| | T1R | Rvs | 5'-GTTTCTACAGACTGG GGATGGATGGTT-3' | (SEQ ID NO: 13) | 0 bp (GSTT1*null) |

In one embodiment, the invention is a method including the steps of obtaining a sample of genomic DNA and conducting three separate PCR runs of portions of the sample. After this, the alleles may be detected. In one embodiment of the invention, a first portion of the sample is amplified by PCR with primers for GSTM1 and CDK2; a second portion is amplified with primers for GSTT1 and GSTM3; and a third portion of the sample is amplified with primers for GSTP1. Following this, the alleles may be detected. In the above method, at least one of the primers used further has a fluorescent such as TET, FAM(6FAM), 5FAM, TAMRA, HEX, R110, JOE, RG6, NED, ROX (Applied Biosystems, Foster City, Calif.). Further, the PCR products of the amplification of the first, second, and third portions of the sample are combined prior to the step of detecting the presence and the gene dosage of the alleles. This detection step may be accomplished by conducting a gel electrophoresis of the sample using a single lane. This allows cost savings over traditional methods. The detection step may next involve fluorescence detection to determine the presence of PCR products for the specific alleles. In addition, the detection step may further involve comparing the areas under the peak of GSTM1*A or GSTM1*B PCR products with the area under the peak of the CDK2 PCR products to determine the gene dosage of GSTM1; as well as comparing the areas under the peak of the GSTM3*A or GSTM3*B PCR products with the area under the peak of the GSTT1 PCR products in order to determine the gene dosage of GSTT1.

The detection step noted above may be varied significantly within the scope of the instant invention. In some forms of the invention, capillary electrophoresis is used in the place of typical gel electrophoresis, followed by fluorescence detection to determine the presence of PCR products for the specific alleles and comparison of the areas under the peak of the GSTM1*A or GSTM1*B PCR products with the area under the peak of the CDK2 PCR products to determine the gene dosage of GSTM1 and comparison of the areas under the peak of the GSTM3*A or GSTM3*B PCR products with the area under the peak of the GSTT1 PCR products to determine the gene dosage of GSTT1.

In other forms of the method of the instant invention, the primers include internally-biotinylated nucleotides. In these methods, the step of detecting the presence and gene dosage of the alleles comprises the steps of combining the PCR products of the amplification of the first, second, and third portions of the sample; exposing the mixture to streptavidin-coated magnetic or non-magnetic beads; and detecting the presence or absence of allele-specific PCR products through the use of a microplate reader capable of indicating the presence or absence of allele-specific PCR products.

Other forms of the invention utilize real-time PCR to amplify and detect the alleles of GSTM1, GSTM3, GSTT1, and GSTP1. This method is useful due to its relative ease and simplicity and its ability to amplify and detect the alleles and determine the gene dosages of GSTM1 and GSTT1 alleles all at the same time and without using specialized equipment, excepting the real time PCR machine itself.

In other forms, the method includes primers that include at least one radiolabeled nucleotide and uses methods known in the art for detecting the radiolabeled molecules, including electrophoresis followed by autoradiography or phosphoimaging and related techniques.

In other embodiments of the invention, it is a high-throughput assay for the detection of glutathione S-transferase polymorphic alleles comprising the steps of: obtaining a sample of genomic DNA, conducting PCR amplification of the genomic DNA using primers for GSTM1, CDK2, GSTT1, GSTM3, and GSTP1; combining the PCR reaction products into one mixture; and detecting the presence and the gene dosage of the alleles. Here, the primers may further include labels such as: fluorescent nucleotide dyes (TET, FAM(6FAM), 5FAM, TAMRA, HEX, R110, JOE, RG6, NED, ROX)(Applied Biosystems, Foster City, Calif.), biotinylated deoxynucleotides, radioactive phosphorus deoxynucleotides, or radioactive sulfur phosporothioates, and others that could function properly in this application. The detection step also involves loading the mixture into a single gel lane and conducting gel electrophoresis or capillary electrophoresis.

A presently preferred embodiment of the instant invention is a method of identifying the alleles of glutathione S-transferase present in a sample of genetic material which includes three distinct PCR steps which may be performed in any order. A first step is to conduct the PCR amplification of the GSTM1 alleles and CDK2 present in a first portion of a genetic sample using primers comprising polynucleotide sequences substantially identical to SEQ ID NO: 1, nucleotides 3–23 of SEQ ID NO: 2, nucleotides 9–31 of SEQ ID NO: 3, SEQ ID NO: 14, and SEQ ID NO: 15; wherein at least one of said primers further comprises a signal marker. A second step is to conduct the PCR amplification of the GSTT1 and GSTM3 alleles present in a second portion of the sample using primers comprising polynucleotide sequences substantially identical to nucleotides 7–26 of SEQ ID NO: 4, nucleotides 7–26 of SEQ ID NO: 5, SEQ ID NO: 12, and nucleotides 6–27 of SEQ ID NO: 13; wherein at least one of said primers further comprises a signal marker. A third step is to conduct the PCR amplification of the GSTP1 alleles present in a third portion of the sample using primers comprising polynucleotide sequences substantially identical to nucleotides 7–25 of SEQ ID NO: 6, nucleotides 10–28 of SEQ ID NO: 7, nucleotides 6–23 of SEQ ID NO: 8, nucleotides 4–21 of SEQ ID NO: 9, SEQ ID NO: 10, and nucleotides 7–25 of SEQ ID NO: 11; wherein at least one of said primers further comprises a signal marker. The detection step follows these amplification steps, and shows the presence or absence of the alleles of GSTM1, GSTM3, GSTT1, and GSTP1, and the gene dosage of GSTM1 and GSTT1.

As with other embodiments, the signal marker of those primers which have markers such as fluorescent dyes (TET, FAM(6FAM), 5FAM, TAMRA, HEX, R110, JOE, RG6, NED, ROX) (Applied Biosystems, Foster City, Calif.), biotinylated deoxynucleotides, radioactive phosphorus deoxynucleotides, or radioactive sulfur phosporothioates, and may include other suitable markers. Also, in some of the methods, the PCR products of the amplification steps are combined prior to the step of detecting the presence of the alleles of GSTM1, GSTM3, GSTT1, and GSTP1, and the gene dosage of GSTM1 and GSTT1. Further, this step may simply comprise analyzing the allele makeup and gene dosage of the sample using a single lane of a gel electrophoresis. This step could also be detecting the presence of the alleles of GSTM1, GSTM3, GSTT1, and GSTP1, and the gene dosage of GSTM1 and GSTT1 using capillary electrophoresis.

In other forms of the instant invention, the primers may additionally comprise internally-biotinylated nucleotides. In these, the step of detecting the presence and gene dosage of the alleles includes the steps of combining the PCR products of the amplification of the first, second, and third portions of the sample; exposing the resulting mixture to streptavidin-coated magnetic or non-magnetic beads; and detecting the presence or absence of allele-specific PCR products through the use of a microplate reader capable of indicating the presence or absence of allele-specific PCR products.

In still other forms of the invention, the steps of amplifying a first portion of the sample with primers for GSTM1 and CDK2; amplifying a second portion of the sample with primers for GSTT1 and GSTM3; amplifying a third portion of the sample with primers for GSTP1; and detecting the presence and the gene dosage of the alleles are accomplished using real-time PCR, wherein amplification and detection of alleles is conducted simultaneously. In some of these embodiments, the signal markers comprise radiolabeled nucleotides. In these, the step of detecting the presence of the alleles of GSTM1, GSTM3, GSTT1, and GSTP1, and the gene dosage of GSTM1 and GSTT1 comprises detecting the radiolabeled PCR products.

Further, in some embodiments, the instant invention is a novel PCR primer comprising a nucleotide sequence selected from the group of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, and SEQ ID NO: 13. In some of these, the PCR primer further includes a signal marker selected such as fluorescent dyes (TET, FAM (6FAM), 5FAM, TEA, HEX, R110, JOE, RG6, NED, ROX) (Applied Biosystems, Foster City, Calif.). These primers may further comprise radiolabeled nucleotides and/or internally-biotinylated nucleotides and/or nucleotide analogs within the scope of the invention.

BRIEF DESCRIPTION OF THE DRAWING

In order that the invention may be more readily understood, a more particular description of the invention briefly described above will be rendered by reference to specific embodiments thereof which are illustrated in the appended drawing. Understanding that this drawing depicts only typical embodiments of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

Figure 1:
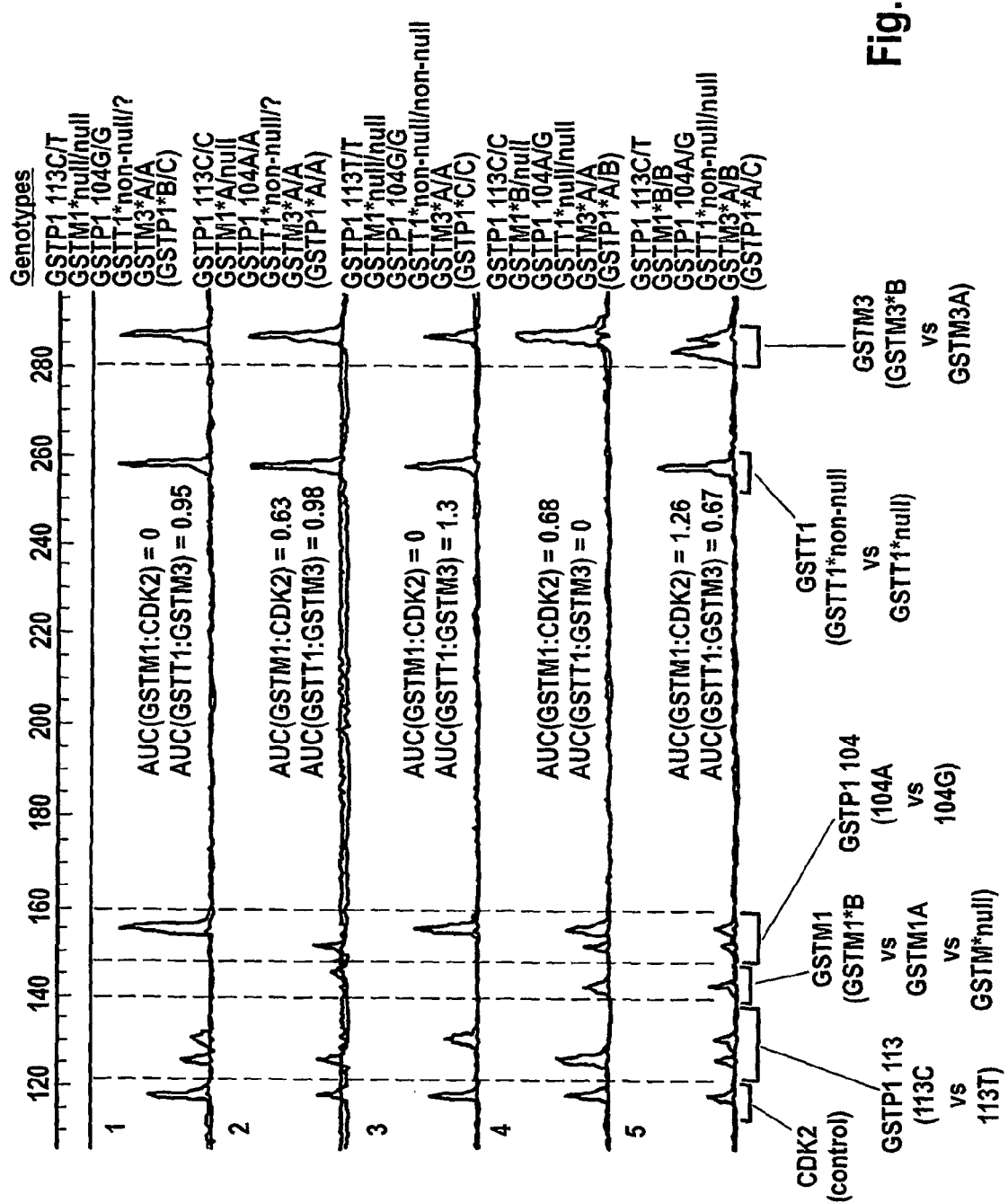
FIG. 1 shows the result of the high-throughput GST polymorphic allele assay of the instant invention for five DNA samples taken from five different human cell lines.

Polymorphisms of glutathione S-transferase (GST) enzymes have been correlated with clinically significant changes of risk for many different cancers. Specifically, cancer risk differences have been associated with polymorphic alleles of GSTM1, GSTM3, GSTP1, and GSTT1. See e.g., Krajinovic et al., *Blood*, 93:1496–1501 (1999), Jahnke et al., *Am. J. Surg.*, 172:671–673 (1996), Volm et al., *Med. & Ped. Onc.*, 28:117–126 (1997), and Elexpuru-Camiruaga et al., *Canc. Res.*, 55:4237–4239 (1995). Differences in response, toxicity, and outcome of treatment for cancer have been associated with polymorphic alleles of GSTM1 and GSTP1. See e.g., Goto et al., *Canc. Res.* 56:3725–3730 (1996), and Volm et al., *Med. & Ped. Onc.*, 28:117–126 (1997). These and other studies conducted on this topic are retrospective studies, however, and thus prospective examinations of risk and response through national trials should lead to the discovery of better-defined relationships between the possible GST genotypes and cancer and cancer treatment success levels.

GST polymorphic alleles occur at frequencies of at least 2.4–20%, and may be as high as 40–84%. This fact alone renders them socially and medically important. The frequencies of these alleles vary among diverse ethnic groups, as seen in Tables 2, 3, 4, and 5 below. Table 2 contains statistics regarding the GSTM1 polymorphic allele frequency in diverse ethnic groups. The number of patients examined in each ethnic group is designated as "n". GSTM1*null is designated as "null." GSTM1*A and GSTM1*B are designated as M1*A and M1*B respectively.1

TABLE 2

GSTM1 Polymorphic Allele Frequencies among Diverse Ethnic Groups

| Ethnic Group | (n) | Null: null | Null: M1*A; Null: M1*B; M1*A/M1*B; or M1*A/M1*B |
|---|---|---|---|
| Multinational | 253 | 50 | 50 |
| Washington Co., MD (caucasians) | 110 | 64.5 | 35.5 |
| African-Americans | 59 | 40.7 | 59.3 |
| Quebec, Canada | 174 | 64.9 | 35.1 |
| United Kingdom | 84 | 44 | 66 |
| United Kingdom | 300 | 57.3 | 42.7 |
| England | 113 | 63.7 | 56.3 |
| Finland | 142 | 43.7 | 56.3 |
| Berlin, Germany | 400 | 50.7 | 49.3 |
| Parma, Italy | 98 | 50 | 50 |
| Linxian County, China | 45 | 53 | 47 |
| Taiwan | 150 | 63.3 | 36.7 |

Table 3 shows GSTM3 polymorphic allele frequencies in two populations from Great Britain. The number of patients examined in each population is designated as "n". M3*A indicates a GSTM3*A allele, and M3*B indicates a GSTM3*B allele.

TABLE 3

GSTM3 Polymorphic Allele Frequencies

| Ethnic Group | (n) | M3*A | M3*B | M3*A: M3*A | M3*A: M3*B | M3*B: M3*B |
|---|---|---|---|---|---|---|
| Great Britain | 244 | 84.2 | 15.8 | 70.9 | 25.8 | 3.4 |
| Great Britain | 300 | | | 73.7 | 21.3 | 5.0 |

Table 4 shows GSTP1 polymorphic allele frequencies among diverse ethnic groups from all over the world. The number of patients examined in each ethnic group is designated as "n". P1*A, P1*B, and P1*C indicate GSTP1*A GSTP1*B GSTP1*C alleles respectively.

TABLE 4

GSTP1 Polymorphic Allele Frequencies among Diverse Ethnic Groups

| Ethnic Group | (n) | P1*A | P1*B | P1*B or P1*C | P1*C |
|---|---|---|---|---|---|
| African-American | 112 | 56.6–58% | 39.9% | | 2.1–5% |
| European | 199 | 61.4% | 31.6% | | 2.4% |
| Scottish | 155 | 72.3% | | 27.7% | |
| Norwegian | 297 | 71.2% | | 28.8% | |
| German Caucasian | 180 | 69.5% | | 30.5% | |
| Indian | 40 | 66.4% | 24.6% | | 2.4% |
| Chinese | 49 | 80.2% | 18.8% | | 0.2% |
| Linxian County, China | 36 | 76.5% | | 23.5% | |
| Japanese | 164 | 83.5% | | 16.5% | |
| Aborigninese | 45 | 89% | 11% | | 0% |

Finally, Table 5 shows GSTT1 polymorphic allele frequencies among diverse ethnic groups from all over the world. The number of patients examined in each ethnic group is designated as "n". GSTT1*null is indicated by "null." "T1" indicates a GSTT1 allele.

TABLE 5

GSTT1 Polymorphic Allele Frequencies among Diverse Ethnic Groups

| Ethnic Group | (n) | Null:null | Null:T1 or T1:T1 |
|---|---|---|---|
| USA | 190 | 16 | 84 |
| Washington Co., MD | 110 | 27.2 | 72.7 |
| African-American | 119 | 21.8 | 78.2 |
| African-Americans | 59 | 28.8 | 71.2 |
| Mexican-American | 73 | 9.7 | 90.3 |
| French Canadian | 176 | 15.9 | 84.1 |
| United Kingdom | 494 | 18.4 | 81.6 |
| Sweden | 270 | 9.6 | 90.4 |
| Australia | 94 | 19 | 81 |
| Chinese | 45 | 64.4 | 35.6 |
| Linxian County, China | 45 | 49 | 51 |
| Korean | 103 | 60.2 | 39.8 |
| Japanese | 126 | 44.4 | 55.6 |

The assay design of the instant invention has four advantages over existing high-throughput assays. Because most GST genotyping assays currently known in the art are solely PCR-based, it has not been possible for investigators to determine gene dosage in the course of the assay. Gene dosage denotes an evaluation of whether one or both alleles were present when a PCR product suggested the presence in the genotype of at least one non-null allele. Further, these assays generally do not differentiate between the non-null GSTM1 alleles (GSTM1*A and GSTM1*B). Most of these examinations further require the additional step of digesting the PCR products with restriction endonucleases in order to determine the genotype.

A first step in the method is to assay for the three polymorphic alleles of GSTM1. The GSTM1 class includes the GSTM1*null, GSTM1*A, and GSTM1*B allelic variants. Fryer et al., *Biochem. J.*, 295:313–315 (1993). GSTM1*null is thought to result from an unequal crossing-over at a duplicated region between the GSTM1 and the GSTM2 loci. Pearson et al., *Am. J. Hum. Genet.*, 53:220233 (1993); and Xu et al., *J. Biol. Chem.*, 273:3517–3527 (1998). As with other null alleles, this one produces no usable product and thus exists as a functional genetic recessive. GSTM1*A and GSTM1*B are polymorphic alleles commonly thought to result from a C to G substitution at codon 173. This change results in a change from the $Lys^{173}$ of GSTM1*A to the $Asn^{713}$ of GSTM1*B. This change alters a hinge region between alpha helices which is involved in GSTM1 dimerization. The polymorphic alleles of Glutathione S-0Transferase Genes are summarized in Table 6.

TABLE 6

Polymorphic Alleles of Glutathione S-Transferase Genes

| Class/ Subclass | Locus | Allelic Variants | Codon | Significance |
|---|---|---|---|---|
| Mu GSTM1 | 1p13.3 | GSTM1*null | | Absent Allele |
| | | GSTM1*A | $Lys^{173}$ | Hinge between to alpha helixes at |
| | | GSTM1*B | $Asn^{173}$ | dimerization site |
| GSTM3 | 1P13.3 | GSTM3*A | Full Intron 6 | Unknown; the |
| | | GSTM3*B | 3bp Deletion in Intron 6 | deletion generates a YY1 Negative Transcription Factor Recognition Site |
| Pi GSTP1 | 11q13 | GSTP1*A | $Ile^{104}$(104a), $Ala^{113}$(113C) | Modified contacts at the binding site |
| | | GSTP1*B | $Val^{104}$(104G), $Ala^{113}$(113C) | for electrophilic carcinogens (H-site) |
| | | GSTP1*C | $Val^{104}$(104G), $Val^{113}$(113T) | |
| Theta GSTT1 | 22q11 | GSTT1*null GSTT1*T1 | | Absent Allele |

Possible GSTM1 genotypes are GSTM1*A/GSTM1*A, GSTM1*A/GSTM1*B, GSTM1*/B/GSTM1*B, GSTM1*A/GSTM1*null, GSTM1*B/GSTM1*null, and GSTM1*null/GSTM1*null.

In the assay method of the instant invention, GSTM1 alleles can be detected by fluorescent, allele-specific PCR using two forward primers, M1FA (SEQ ID NO: 1) and M1FB (SEQ ID NO: 2), and one reverse primer, M1R (SEQ ID NO: 3). The sequences of these primers are as follows:

M1FA: 5'-(TET)TTGGGAAGGCGTCCAAGCAC-3'

M1FB: 5'-(FAM)TCTTTGGGAAGGCGTCCAAGCAG-3'

M1R: 5'-GTTTCTTCTGCTTCACGTGTTATGAAGGTTC-3'

The polymorphic nucleotides in the primers are placed on the 3' side of the forward primers in order to increase sequence specificity of PCR amplification. TET and FAM represent green and blue fluorescent tags, respectively. The boxed sequence of M1FB represents a non-sequence specific tail added to create PCR product length differences between the 142 base pair TET-tagged GSTM1*A PCR product and the 145 base pair FAM-tagged GSTM1*B PCR product. The boxed sequence of the reverse primer was added to prevent spectral overlap between TET- and FAM-tagged PCR products. Both the length of the non-sequence specific tails and the tags may be easily varied within the scope of the instant invention.

CDK2 is co-amplified as a positive control for GSTM1*null/GSTM1*null genotypes and to determine GSTM1 gene dosage. CDK2 forward and reverse primers are CDK2F (SEQ ID NO: 14) and CDK2R (SEQ ID NO: 15), respectively. Sequences of CDK2F and CDK2R are as follows:

```
CDK2F:    5'-CCTATTCCCTGGAGATTCTG

CDK2R:    5'-(FAM)AAACTTGGCTTGTAATCAGGC
```

To determine gene dosage of GSTM1*A or GSTM1*B by competitive PCR, peak areas of GSTM1*A or GSTM1*B, and CDK2 PCR products can be quantified by polyacrylamide gel electrophoresis and fluorescence detection using an ABI PRISM® 373 Sequence Detection System (Applied Biosystems, Foster City, Calif.). Peak areas of GSTM1*A or GSTM1*B products can them be compared to the peak area of the CDK2 PCR product in order to determine GSTM1 gene dosage, thereby differentiating between the genotypes GSTM1*A/GSTM1*A and GSTM1*B/GSTM1*B and the genotypes GSTM1*A/GSTM1*null or GSTM1*B/GSTM1*null.

This step may be carried out under the following reaction or other suitable conditions: CDK2F 0.25 µM, M1R 0.5 µM, Taq Platinum Polymerase 0.25 U (Life Technologies, Rockville, Md.), spermidine HCl 0.2 mM, MgCl$_2$ 1.5 mM, NaCl 40 mM, Tris-HCl (pH 8.3) 10 mM, dNTPs 200 µM each. Reaction volume is 20 µl. Samples are amplified in an MJResearch PTC250 Thermacycler (MJResearch, Inc., Watertown, Mass.) or other suitable equipment. The amplification parameters can be as follows: denaturing for 5 minutes at 94 C, 25 temperature cycles (comprising 20 seconds at 94 C, 20 seconds at 52 C, and 40 seconds at 72 C), followed by a final extension for 10 minutes at 72 C.

A next step in the assay method is assaying for the polymorphic alleles of GSTM3. This subgroup includes the GSTM3*A and GSTM3*B allelic variants. These alleles are thought to result from a 3 base-pair deletion in intron 6 which generates a YY1 negative transcription factor recognition site in GSTM3*B that does not exist in GSTM3*A. Possible genotypes include GSTM3*A/GSTM3*A, GSTM3*A/GSTM3*B, and GSTM3*B/GSTM3*B.

In the assay of the instant invention, GSTM3 alleles may be detected by fluorescent, allele-specific PCR using one forward primer, M3F (SEQ ID NO: 4) and one reverse primer, M3R (SEQ ID NO: 5). The sequences for these primers are as follows:

```
M3F:    5'-(FAM)GTTTCT CCTCAGTACTTGGAAGAGCT-3'

M3R:    5'-GTTTCT CACATGAAAGCCTTCAGGTT-3'
```

The three base pair deletion for GSTM3*B is located internal to the primers M3F and M3R. The boxed sequences represent non-sequence specific tails added to adjust PCR product length. Amplification of GSTM3*A results in a 287 base pair PCR product.

This amplification step is compatible with, and thus may be performed concurrently with, GSTT1 PCR amplification. One suitable set of reaction conditions follow: T1F 0.5 µM, T1R 0.5 µM, M3FA 0.5 µM, M3FB 0.5 µM, M3R 0.5 µM, Tag Platinum Polymerase 0.25 U (Life Technologies, Rockville, Md.), spermidine HCl 0.2 mM, MgCl$_2$ 1.5 mM, NaCl 40 mM, Tris-HCl (pH 8.3) 10 mM, and dNTPs 200 µM each. Reaction volume is 20 µl. Samples are amplified in an MJResearch PTC250 Thermacycler (MJResearch Inc., Watertown, Mass.) or other suitable equipment. The amplification may occur under the following sample conditions: denaturing for 5 minutes at 94 C, 25 temperature cycles (20 seconds at 94 C, 20 seconds at 58 C, 40 seconds at 72 C), followed by a final extension for 10 minutes at 72 C. Other suitable amplification reaction systems will be understood by one of skill in the art.

A third step is the detection of the polymorphic alleles of GSTP1. These include GSTP1*A, GSTP1*B, GSTP1*C, and GSTP1*D. The GSTP1*D allele has been observed, but only in very rare circumstances in two individuals. Watson et al., *Carcinogenesis*, 19:275–280 (1998). The GSTP1 polymorphic alleles are thought to result from A to G and C to T transitions at nucleotides +313 of exon 5 and +341 of exon 6. These transitions result in ATC (Ile$^{104}$) to GTC (Val$^{104}$) and GCG (Ala$^{113}$) to GTG (Val$^{113}$). Specifically, GSTP1*A codon 104 is ATC, coding for Ile$^{104}$, and codon 113 is GCG, for Ala$^{113}$. GSTP1*B codon 104 is GTC, coding for Val$^{104}$, and codon 113 is GCG for Ala$^{113}$. GSTP1*C codon 104 is GTC, coding for Val$^{104}$, and codon 113 is GTG for Val$^{113}$. GSTP1*D codon 104 is ATC, coding for Ile$^{104}$, and codon 113 is GTG for Val$^{113}$. GSTP1 genotypes expected to be common include GSTP1*A/GSTP1*A, GSTP1*A/GSTP1*B, GSTP1*A/GSTP1*C, GSTP1*B/GSTP1*B, GSTP1*B/GSTP1*C, GSTP1*C/GSTP1*C.

The assay of the instant invention detects polymorphisms at codon 104 of GSTP1 by fluorescent, allele-specific PCR using two forward primers, P1-104FA (SEQ ID NO: 6) and P1-104FG (SEQ ID NO: 7), and one reverse primer, P1-104R (SEQ ID NO: 8). The sequences for these primers are as follows:

```
P1-104FA:   5'-(FAM)GTTTCT GACCTCCGCTGCAAATACA-3'

P1-104FG:   5'-(TET)GTTTCTCTT GACCTCCGCTGCAAATACG-3'

PO1-104R:   5'-GTTTC TCAGCCCAAGCCACCTGA-3'
```

As noted with GSTM1 above, the underlined polymorphic nucleotides are placed at the 3' side of the forward primers in order to increase sequence specificity of PCR amplification. The boxed sequences represent non-sequence specific tails added to adjust PCR product length and to create differences in length between PCR products containing an A in codon 104, (thus producing a 150 base pair PCR product) and products containing a G in codon 104 (thus producing a 153 base pair PCR product). Both the length of the non-sequence specific tails and the tags may be easily varied within the scope of the instant invention.

The reaction for this assay at codon 104 may proceed as follows or under other suitable reaction conditions: P1-104FA at 0.25 µM, P1-104FG 0.125 µM, P1-104R 0.5 µM, Taq Platinum Polymerase 0.25 U (Life Technologies, Rockville, Md.), spermidine HCl 0.2 mM, MgCl$_2$ 1.5 mM, NaCl 40 mM, Tris-HCl (pH 8.3), 10 mM, dNTPs 200 µM each. The reaction volume is 20 µl. Samples can be amplified in an MJResearch PTC250 Thermacycler (MJResearch Inc., Watertown, Mass.) or with other suitable equipment. The amplification may occur under the following conditions: denaturing for 5 minutes at 94 C, 25 temperature cycles (20 seconds at 94 C, 20 seconds at 64 C, 40 seconds at 72 C), followed by a final extension for 10 minutes at 72 C.

Polymorphisms of codon 113 of GSTP1 are similarly detected by fluorescent, allele-specific PCR using two forward primers, P1-113FC (SEQ ID NO: 9) and P1-113FT (SEQ ID NO: 10), and one reverse primer, P1-113R (SEQ ID NO: 11). The sequences for these primers are as follows:

| P1-113FC: | 5'-(TET)CTTTGGTGTCTGGCAGGAGGT-3' |
|---|---|
| P1-113FT: | 5'-(FAM)GGTGTCTGGCAGGAGGC-3' |
| P1-113R: | 5'-GTTTCTTGGTCTCCCACAATGAAGG-3' |

The underlined polymorphic nucleotides are placed at the 3' side of the forward primers in order to increase sequence specificity of PCR amplification. The boxed sequences represent non-sequence specific tails added to adjust PCR product length and to create differences in length between PCR products containing a C in codon 113 (producing a 130 base pair PCR product), and those containing a T in codon 113 (producing a 126 base pair PCR product). Both the length of the non-sequence specific tails and the tags may be easily varied within the scope of the instant invention.

One suitable set of reaction conditions for this step are as follows: P1-113FC 0.25 µM, P1-113FT 0.125 µM, P1-113R 0.5 µM, Taq Platinum Polymerase 0.25 U (Life Technologies, Rockville, Md.), spermidine HCl 0.2 mM, MgCl$_2$ 1.5 mM, NaCl 40 mM, Tris-HCl (pH 8.3) 10 mM, dNTPs 200 µM each. Reaction volume is 20 µl. Samples may be amplified in an MJResearch PTC250 Thermacycler (MJResearch Inc., Watertown, Mass.) or other suitable equipment. The amplification may occur under the following reaction conditions: denaturing for 5 minutes at 94 C, 25 temperature cycles (20 seconds at 94 C, 20 seconds at 64 C, 40 seconds at 72 C), followed by a final extension for 10 minutes at 72 C.

A final step in the first portion of the assay of the instant invention is to detect the polymorphic alleles of GSTT1, including GSTT1*null and GSTT1. As with the other null allele noted above, the GSTT1*null allele produces no functional product, thus operating as a recessive allele. Possible genotypes include GSTT1*T1/GSTT1*T1, GSTT1*T1/GSTT1*null, and GSTT1*null/GSTT1*null.

GSTT1 alleles are detected by fluorescent, allele-specific PCR using the forward primer T1F (SEQ ID NO: 12), and T1R (SEQ ID NO: 13). The sequences of these primers are as follows:

| T1F: | 5'-(FAM)TTCCTTACTGGTCCTCACATCTC-3' |
|---|---|
| T1R: | 5'-GTTTCTACAGACTGGGGATGGATGGTT-3' |

The boxed sequence of T1R represents a non-sequence specific tail added to adjust PCR product length. GSTT1 is amplified with GSTM3 as a positive control for GSTT1*null/GSTT1*null genotypes and to determine GSTT1 gene dosage. GSTM3 forward and reverse primers were used as specified above. Both the length of the non-sequence specific tails and the tags may be easily varied within the scope of the instant invention.

To determine gene dosage of GSTT1 by competitive PCR, peak areas of GSTM3*A or GSTM3*B, and GSTT1 PCR products are quantified by polyacrylamide gel electrophoresis and fluorescence detection using an ABI PRISM® 373 Sequence Detection System (Applied Biosystems, Foster City; CA). Peak areas of GSTM3*A or GSTM3*B products are compared to the peak area of the GSTT1 PCR product in order to determine GSTT1 gene dosage, thereby differentiating between the genotypes GSTT1*T1/GSTT1*T1 and GSTT1*null/GSTT1*null.

Sample reaction conditions that can be used are as follows: T1F 0.5 µM, T1R 0.5 µM, M3FA 0.5 µM, M3R 0.5 µM, Taq Platinum Polymerase 0.25 U (Life Technologies, Rockville, Md.), spermidine HCl 0.2 mM, MgCl$_2$1.5 mM, NaCl 40 mM, Tris-HCl (pH 8.3) 10 mM, dNTPs 200 µM each. Reaction volume is 20 µl. Samples are amplified in an MJResearch PTC250 Thermacycler (MJResearch Inc., Watertown, Mass.) or other suitable equipment. A suitable set of reaction conditions for the PCT amplification are as follows: denaturing for 5 minutes at 94 C, 25 temperature cycles (20 seconds at 94 C, 20 seconds at 58 C, 40 seconds at 72 C), followed by a final extension for 10 minutes at 72 C.

A final step of the instant assay is to combine the PCR products of each of the PCR reactions above. Following this, the PCR reactants may then be loaded into a single lane on an ABI PRISM® 373 Sequence Detection System (Applied Biosystems, Foster City, Calif.). For this study, interpretation was performed manually although automated determination of GST genotypes is possible with ABI PRISM® software.

Referring to FIG. 1, the results of a high throughput genotyping conducted according to the method of the present invention is shown. The rows 1–5 each represent DNA samples from different human cell lines. The genotype of each DNA sample was determined by the differential length of PCT products (increasing from left to right). Alleles are represented from left to right in the following order: CDK2 (a control), GSTP1 113C, GSTP1 113T, GSTM1*B, GSTM1*A, GSTM1*null, GSTP1 104A, GSTP1 104G, GSTT1*non-null, GSTT1*NULL, GSTM3B, AND GSTM3*A. The GSTP1 genotype designations GSTP1*A, GSTP1*B, and GSTP1*C were determined by the combination of GSTP1 113 AND GSTP1 104 genotypes as follows: GSTP1*A=113C/104A, GSTP1*B=113C/104G, and GSTP1*C=113T/104G. Gene dosage for GSTM1 AND GSTT1 was determined by comparing the area under the curve (AUC) of their products to the AUC of co-amplified homozygous controls CDK2 and GSTM3, respectively. AUC ratios are near linear, but may require optimization with the first set of patient samples.

Specifically, the genotype results are shown for five separate cell-line-derived DNA samples. Each line represents four different, combined PCR reactions from a single DNA sample source. The genotype corresponding to each sample is shown at the end of each line. The gene dosage for GSTM1 was determined by examining the ratios of the peak area under the curve of GSTM1 vs. CDK2. The gene dosage for GSTT1 was determined by examining the ratios of the peak area under the curve of GSTT1 vs. GSTM3. Ratios greater than 1.0 were interpreted to represent genotypes GSTM1*non-null/GSTT1*null. Independent experiments verifying GSTM1 and GSTT1 gene dosage by an independent long range PCR assay.

Though the data in FIG. 1 was gathered using DNA gathered from tissue-culture cell lines, the assay method has been shown successful in assaying DNA derived from patient-derived peripheral leukocytes. It is further useful in analyzing DNA isolated from buccal epithelial cells (taken in some instances from mouthwash samples) as well as dried blood spots taken from Guthrie cards. This characteristic of sample source versatility renders the assay method of the instant review highly useful for large clinical trials.

Finally, the design and cost of the high-throughput assay method of the instant invention render it attractive to researchers. More specifically, the methodology of the instant invention allows the determination of polymorphic alleles of four different GST genes for 96 patient samples within a period of about 10 hours at a current cost of approximately $7.50 per sample.

As a result of these characteristics of the instant invention, it is apparent that the method of the instant invention lends itself to a wide array of applications. These include the pharmacogenetic applications of: detecting individuals at risk for specific diseases in order to aid in the development of prevention strategies, tailoring therapeutic regimens for patients predicted to have decreased therapeutic response to medical therapy, tailoring therapeutic regimens for patients predicted to have increased therapy-related toxicity, and allowing for the patient-specific utilization of allele-specific small-molecule inhibitors for the purpose of reversing chemotherapy resistance among cancers over-expressing certain GST polymorphic alleles.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims that follow this specification are to be embraced within their scope.

The invention claimed is:

1. A method of detecting the presence of glutathione S-transferase alleles comprising the steps of:
   obtaining a sample of genomic DNA;
   amplifying a first portion of the sample with primers for GSTM1 and CDK2;
   amplifying a second portion of the sample with primers for GSTT1 and GSTM3;
   amplifying a third portion of the sample with primers for GSTP 1; and
   detecting the alleles and their gene dosage; wherein said detecting shows the presence or absence of the alleles of GSTM1, GSTM3, GSTT1, and GSTP1, wherein said GSTM1 alleles are GSTM1*null, GSTM1*A, and GSTM1*B, wherein said GSTM3 alleles are GSTM3*A and GSTM3*B, wherein said GSTT1 alleles are GSTT1*null and GSTT1*T1, and said GSTP1 alleles are GSTP1*A GSTP 1*B, GSTP1*C and GSTP1*D, and wherein said detecting shows the gene dosages of GSTM1 and GSTT1 alleles.

2. The method of claim 1, wherein at least one primer further comprises a fluorescent tag selected from the group consisting of TET, FAM(6FAM), 5FAM, TAMRA, HEX, R110, JOE, RG6, NED, and ROX.

3. The method of claim 2, wherein PCR products of the amplification of the first, second, and third portions of the sample are combined prior to the step of detecting the presence and the gene dosage of the alleles.

4. The method of claim 3 wherein the step of detecting the presence or absence of the alleles and their gene dosage comprises conducting a gel electrophoresis of the sample using a single lane.

5. The method of claim 4, wherein the step of detecting the presence or absence of the alleles and their gene dosage further comprises fluorescence detection to determine the presence of PCR products for the specific alleles.

6. The method of claim 5, wherein the step of detecting the alleles and their gene dosage further comprises the steps of:
generating peaks corresponding to the presence of the PCR products;
comparing the areas under the peak of GSTM1*A or GSTM1*B PCR products with the area under the peak of CDK2 PCR products to determine the gene dosage of GSTM1 alleles; and
comparing the areas under the peak of GSTM3*A or GSTM3*B PCR products with the area under the peak of GSTT1 PCR products to determine the gene dosage of GSTT1 alleles.

7. The method of claim 3, wherein the step of detecting the alleles and their gene dosage comprises capillary electrophoresis.

8. The method of claim 7, wherein the step of detecting the alleles and their gene dosage further comprises fluorescence detection to determine the presence of PCR products for the specific alleles.

9. The method of claim 8, wherein the step of detecting the alleles and their gene dosage further comprises the steps of:
generating peaks corresponding to the presence of the PCR products:
comparing the areas under the peak of GSTM1*A or GSTM1*B PCR products with the area under the peak of CDK2 PCR products to determine the gene dosage of GSTM1 alleles; and
comparing the areas under the peak of GSTM3*A or GSTM3*B PCR products with the area under the peak of GSTT1 PCR products to determine the gene dosage of GSTT1 alleles.

10. The method of claim 2, wherein the primers further comprise internally-biotinylated nucleotides.

11. The method of claim 10, wherein the step of detecting the presence and gene dosage of the alleles comprises the steps of:
determine the presence of PCR products for the specific alleles;
combining the PCR products of the amplification of the first, second, and third portions of the sample;
exposing the mixture to streptavidin-coated magnetic or non-magnetic beads; and
detecting the presence or absence of allele-specific PCR products through the use of a microplate reader capable of indicating the presence or absence of the PCR products for the specific alleles.

12. The method of claim 2, wherein the steps of amplifying a first portion of the sample with primers for GSTM1 and CDK2; amplifying a second portion of the sample with primers for GSTT 1 and GSTM3; amplifying a third portion of the sample with primers for GSTP 1; and detecting the presence and the gene dosage of the alleles are accomplished using real-time PCR, wherein amplification and detection of the alleles of GSTM1, GSTT1, GSTM3, and GSTP1 and the determination of the gene dosages of GSTM1 and GSTT1 alleles is conducted simultaneously.

13. The method of claim 1 wherein at least one of the primers comprises at least one radiolabeled nucleotide.

14. The method of claim 13, wherein the step of detecting the alleles and their gene dosage comprises detection of the radiolabeled nucleotides.

15. A high-throughput assay for the detection of glutathione S-transferase polymorphic alleles comprising the steps of:
obtaining a sample of genomic DNA;
conducting PCR amplification of the genomic DNA using primers for GSTM 1, CDK2, GSTT1, GSTM3, and GSTP1 to produce PCR reaction products;
combining the PCR reaction products into one mixture; and
detecting the presence and the gene dosage of the alleles of GSTM1, GSTM3, GSTT1, and GSTP1, wherein said GSTM1 alleles are GSTM1*null, GSTM1*A, and GSTM1*B wherein said GSTM3 alleles are GSTM3*A and GSTM3*B, wherein said GSTT1 alleles are GSTT1*null and GSTT1*T1, and said GSTP1 alleles are GSTP1*A, GSTP1*B, GSTP1*C and GSTP1*D.

16. The high-throughput assay of claim 15, wherein at least one of the primers further comprises a label selected from the group consisting of: TET, FAM(6FAM), 5FAM, TAMRA, HEX, R110, JOE, RG6, NED, ROX, biotinylated deoxynucleotides, radioactive phosphorus deoxynucleotides, and radioactive sulfur phosporothioates.

17. The high-throughput assay of claim 16, wherein the step of detecting the presence and the gene dosage of the alleles comprises loading the mixture into a single gel lane and conducting gel electrophoresis.

18. The high-throughput assay of 16, wherein the step of detecting the presence and the gene dosage of the alleles comprises capillary electrophoresis.

19. A method of identifying the alleles of glutathione S-transferase present in a sample of genetic material, comprising the steps of:
conducting the PCR amplification to produce PCR reaction products of the GSTM1 alleles and CDK2 present in a first portion of the sample using primers comprising polynucleotide sequences substantially identical to SEQ ID NO: 1, nucleotides 3–23 of SEQ ID NO: 2, nucleotides 9–31 of SEQ ID NO: 3, SEQ ID NO: 14, and SEQ ID NO: 15; wherein at least one of said primers further comprises a signal marker;
conducting the PCR amplification to produce PCR reaction products of the GSTT1 and GSTM3 alleles present in a second portion of the sample using primers comprising polynucleotide sequences substantially identical to nucleotides 7–26 of SEQ ID NO: 4, nucleotides 7–26 of SEQ ID NO: 5, SEQ ID NO: 12, and nucleotides 6–27 of SEQ ID NO: 13; wherein at least one of said primers further comprises a signal marker;
conducting the PCR amplification to produce PCR reaction products of the GSTP1 alleles present in a third portion of the sample using primers comprising polynucleotide sequences substantially identical to nucleotides 7–25 of SEQ ID NO: 6, nucleotides 10–28 of SEQ ID NO: 7, nucleotides 6–23 of SEQ ID NO: 8, nucleotides 4–21 of SEQ ID NO: 9, SEQ ID NO: 10, and nucleotides 7–25 of SEQ ID NO: 11; wherein at least one of said primers further comprises a signal marker; and
detecting the presence and gene dosage of the alleles amplified above; wherein said detecting shows the presence or absence of the alleles of GSTM1, GSTM3, GSTT1, and GSTP1, wherein said GSTM1 alleles are GSTM1*null, GSTM1*A, and GSTM1*B, wherein said GSTM3 alleles are GSTM3*A and GSTM3*B, wherein said GSTT1 alleles are GSTT1*null and GSTT1*T1, and said GSTP1 alleles are GSTP1*A, GSTP1*B, GSTP1*C and GSTP1*D, and wherein said detecting shows the gene dosage of GSTM1 and GSTT1 alleles.

20. The method of claim 19, wherein the signal markers are selected from the group consisting of: TET, FAM (6FAM), 5FAM, TAMRA, HEX, R110, JOE, RG6, NED, ROX, biotinylated deoxynucleotides, radioactive phosphorus deoxynucleotides, and radioactive sulfur phosorothioates.

21. The method of claim 20, wherein the PCR products of the amplification steps are combined prior to the step of detecting the presence of the alleles of GSTM1, GSTM3, GSTT1, and GSTP1, and the gene dosage of GSTM1 and GSTT1 alleles.

22. The method of claim 21 wherein the step of detecting the presence of the alleles of GSTM1, GSTM3, GSTT1, and GSTP1, and the gene dosage of GSTM1 and GSTT1 comprises analyzing an allele makeup and gene dosage of the sample using a single lane of a gel electrophoresis.

23. The method of claim 21, wherein the step of detecting the presence of the alleles of GSTM1, GSTM3, GSTT1, and GSTP1, and the gene dosage of GSTM1 and GSTT1 comprises capillary electrophoresis.

24. The method of claim 21, wherein the primers further comprise internally-biotinylated nucleotides.

25. The method of claim 24, wherein the step of detecting the presence and gene dosage of the alleles comprises the steps of:

determine the presence of PCR products for the specific alleles;

combining the PCR products of the amplification of the first, second, and third portions of the sample;

exposing the mixture to streptavidin-coated magnetic or non-magnetic beads; and detecting the presence or absence of allele-specific PCR products through the use of a microplate reader capable of indicating the presence or absence of the PCR products for the specific alleles.

26. The method of claim 19, wherein the steps of amplifying a first portion of the sample with primers for GSTM1 and CDK2; amplifying a second portion of the sample with primers for GSTT1 and GSTM3; amplifying a third portion of the sample with primers for GSTP 1; and detecting the presence and the gene dosage of the alleles are accomplished using real-time PCR, wherein amplification and detection of the alleles of GSTM1, GSTT1, GSTM3, and GSTP1 and the determination of the gene dosage of GSTM1 and GSTT1 alleles is conducted simultaneously.

27. The method of claim 19, wherein at least one of the signal markers comprises at least one radiolabeled nucleotide.

28. The method of claim 27, wherein the step of detecting the presence of the alleles of GSTM1, GSTM3, GSTT1, and GSTP1, and the gene dosage of GSTM1 and GSTT1 comprises detecting radiolabeled PCR products.

* * * * *

SEQUENCE LISTING

```
<160> NUMBER OF SEQ ID NOS: 15

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotide.

<400> SEQUENCE: 1
ttgggaaggc gtccaagcac                                              20

<210> SEQ ID NO 2
<211> LENGTH: 23
<212> TYPE: DNA
<213> ORGANISM: Artificial Sequence
<220> FEATURE:
<223> OTHER INFORMATION: Synthetic oligonucleotide.

<400> SEQUENCE: 2
tctttgggaa ggcgtccaag cag                                          23

<210> SEQ ID NO 3
<211> LENGTH: 31
<212> TYPE: DNA
<213> ORGANISM: Artificial Sequence
<220> FEATURE:
<223> OTHER INFORMATION: Synthetic oligonucleotide.

<400> SEQUENCE: 3
gtttcttctg cttcacgtgt tatgaaggtt c                                 31

<210> SEQ ID NO 4
<211> LENGTH: 26
<212> TYPE: DNA
<213> ORGANISM: Artificial Sequence
```

```
<220> FEATURE:
<223> OTHER INFORMATION: Synthetic oligonucleotide.

<400> SEQUENCE: 4
gtttctcctc agtacttgga agagct                                        26

<210> SEQ ID NO 5
<211> LENGTH: 26
<212> TYPE: DNA
<213> ORGANISM: Artificial Sequence
<220> FEATURE:
<223> OTHER INFORMATION: Synthetic oligonucleotide.

<400> SEQUENCE: 5
gtttctcaca tgaaagcctt caggtt                                        26

<210> SEQ ID NO 6
<211> LENGTH: 25
<212> TYPE: DNA
<213> ORGANISM: Artificial Sequence
<220> FEATURE:
<223> OTHER INFORMATION: Synthetic oligonucleotide.

<400> SEQUENCE: 6
gtttctgacc tccgctgcaa ataca                                         25

<210> SEQ ID NO 7
<211> LENGTH: 28
<212> TYPE: DNA
<213> ORGANISM: Artificial Sequence
<220> FEATURE:
<223> OTHER INFORMATION: Synthetic oligonucleotide.

<400> SEQUENCE: 7
gtttctcttg acctccgctg caaatacg                                      28

<210> SEQ ID NO 8
<211> LENGTH: 23
<212> TYPE: DNA
<213> ORGANISM: Artificial Sequence
<220> FEATURE:
<223> OTHER INFORMATION: Synthetic oligonucleotide.

<400> SEQUENCE: 8
gtttctcagc ccaagccacc tga                                           23

<210> SEQ ID NO 9
<211> LENGTH: 21
<212> TYPE: DNA
<213> ORGANISM: Artificial Sequence
<220> FEATURE:
<223> OTHER INFORMATION: Synthetic oligonucleotide.

<400> SEQUENCE: 9
ctttggtgtc tggcaggagg t                                             21

<210> SEQ ID NO 10
<211> LENGTH: 17
<212> TYPE: DNA
<213> ORGANISM: Artificial Sequence
<220> FEATURE:
<223> OTHER INFORMATION: Synthetic oligonucleotide.

<400> SEQUENCE: 10
ggtgtctggc aggaggc                                                  17
```

-continued

<210> SEQ ID NO 11
<211> LENGTH: 25
<212> TYPE: DNA
<213> ORGANISM: Artificial Sequence
<220> FEATURE:
<223> OTHER INFORMATION: Synthetic oligonucleotide.

<400> SEQUENCE: 11
gtttcttggt ctcccacaat gaagg                                   25

<210> SEQ ID NO 12
<211> LENGTH: 23
<212> TYPE: DNA
<213> ORGANISM: Artificial Sequence
<220> FEATURE:
<223> OTHER INFORMATION: Synthetic oligonucleotide.

<400> SEQUENCE: 12
ttccttactg gtcctcacat ctc                                     23

<210> SEQ ID NO 13
<211> LENGTH: 27
<212> TYPE: DNA
<213> ORGANISM: Artificial Sequence
<220> FEATURE:
<223> OTHER INFORMATION: Synthetic oligonucleotide.

<400> SEQUENCE: 13
gtttctacag actggggatg gatggtt                                 27

<210> SEQ ID NO 14
<211> LENGTH: 20
<212> TYPE: DNA
<213> ORGANISM: Artificial Sequence
<220> FEATURE:
<223> OTHER INFORMATION: Synthetic oligonucleotide.

<400> SEQUENCE: 14
cctattccct ggagattctg                                         20

<210> SEQ ID NO 15
<211> LENGTH: 21
<212> TYPE: DNA
<213> ORGANISM: Artificial Sequence
<220> FEATURE:
<223> OTHER INFORMATION: Synthetic oligonucleotide.

<400> SEQUENCE: 15
aaacttggct tgtaatcagg c                                       21